United States Patent [19]

Capelli

[11] 3,958,903
[45] May 25, 1976

[54] POSITIVE DISPLACEMENT DEVICE

[76] Inventor: Raymond A. Capelli, 112-1P Union Road, Spring Valley, N.Y. 10977

[22] Filed: Apr. 26, 1974

[21] Appl. No.: 464,399

Related U.S. Application Data

[63] Continuation of Ser. No. 280,704, Aug. 14, 1972, abandoned.

[52] U.S. Cl. .................................. 417/503; 92/168
[51] Int. Cl.² .................... F04B 39/02; F15B 11/18
[58] Field of Search ............ 417/437, 503; 92/168; 277/165, 168

[56] References Cited
UNITED STATES PATENTS

| | | | |
|---|---|---|---|
| 973,739 | 10/1910 | Alvergant | 417/273 |
| 2,795,195 | 6/1957 | Amblard | 417/437 |
| 3,125,963 | 3/1964 | Whitley et al. | 92/168 |
| 3,145,629 | 8/1964 | Gottzmann | 417/503 |
| 3,162,130 | 12/1964 | Glisson | 417/416 |
| 3,233,554 | 2/1966 | Huber et al. | 92/168 |
| 3,330,217 | 7/1967 | Baur et al. | 92/258 |
| 3,410,477 | 11/1968 | Hartley | 417/534 |
| 3,413,929 | 12/1968 | Cook et al. | 92/168 |
| 3,494,624 | 2/1970 | Woodling | 277/165 |
| 3,549,154 | 4/1969 | Jones | 277/165 |
| 3,636,824 | 1/1972 | Clark | 277/165 |
| 3,663,024 | 5/1972 | Traub | 277/165 |
| 3,679,332 | 7/1972 | Yophe | 417/503 |

Primary Examiner—William L. Freeh
Attorney, Agent, or Firm—Burgess, Dinklage & Sprung

[57] ABSTRACT

A positive displacement device is disclosed and includes
a. a housing defining a fluid intake discharge chamber,
b. a seal housing adjacent the chamber housing,
c. a piston adapted to reciprocate in the seal housing and the fluid intake and discharge chamber,
d. a seal adapted to prevent flow of fluid from the fluid intake and discharge chamber to said seal housing. The seal is adjacent the fluid intake and discharge chamber in the seal housing and has a first ring in positive sliding sealing contact with the piston and a second ring compressively positioned between the first ring and the seal housing to urge the first ring against the piston at a right angle to its direction of travel,
e. means to reciprocate the piston in the fluid intake and discharge chamber and the seal housing, and
f. a valve in communication with the fluid intake and discharge chamber adapted to allow fluid to flow into and/or from the chamber in response to the movement of the piston therein.

6 Claims, 5 Drawing Figures

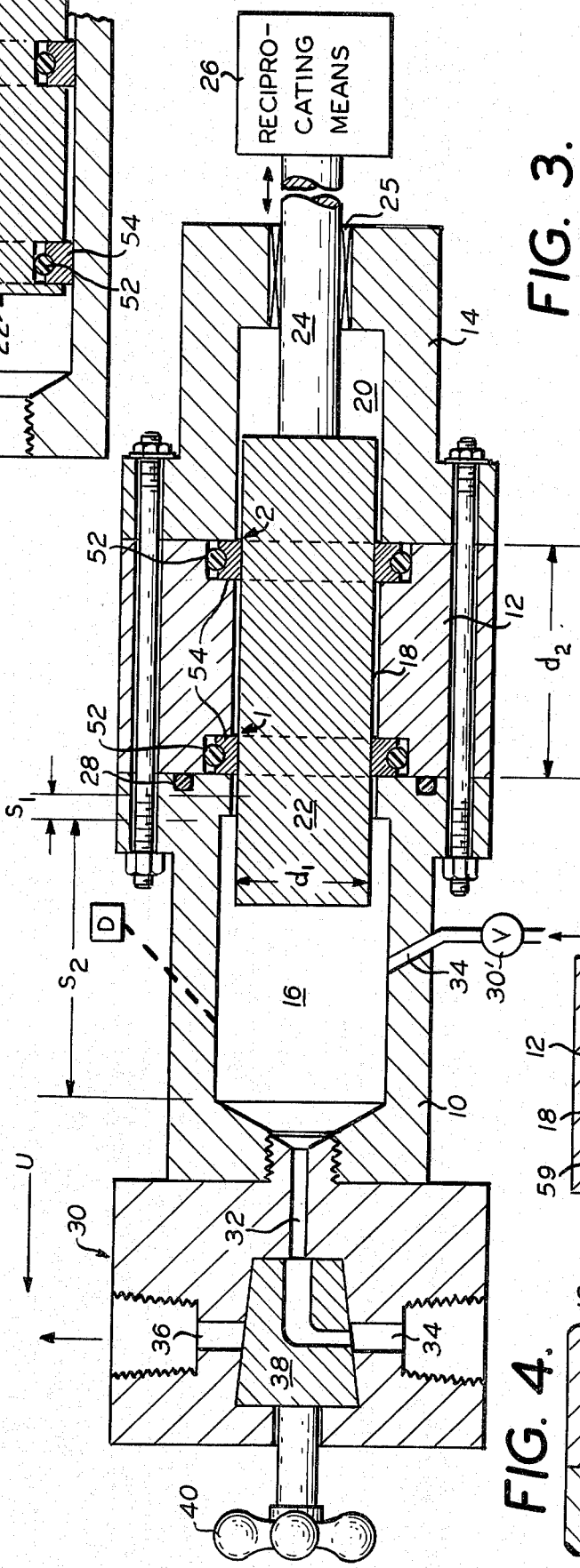
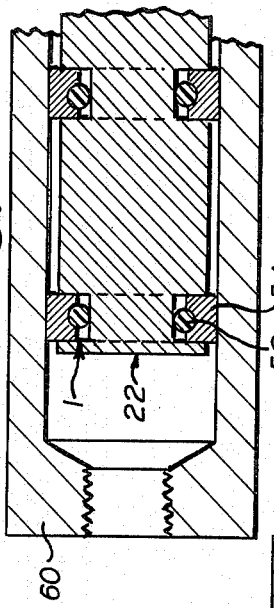
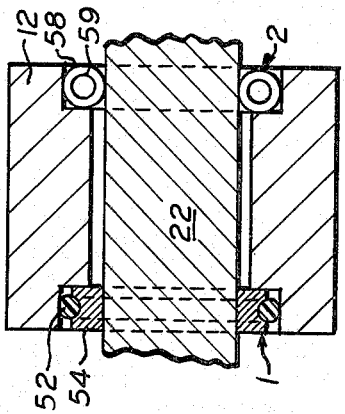
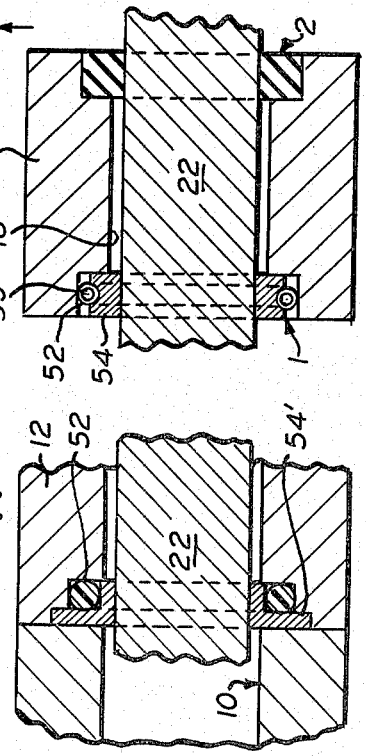

POSITIVE DISPLACEMENT DEVICE

This is a continuation of application Ser. No. 280,704, filed Aug. 14, 1972, now abandoned.

BACKGROUND

This invention relates to a positive displacement device. More particularly, this invention relates to a positive displacement pump or metering device which is capable of dispensing fluids from a source or reservoir at extremely high accuracy by providing seals which prevent the flow of fluid from the dispensing chamber other than in the desired direction for taking the fluid in and discharging same.

Shaft seals for reciprocating pistons and rods which move in a sealed chamber have commonly included a rubber O-ring. Often the O-ring is used in combination with one or more backup rings. The rubber O-ring tangentially contacts the sliding shaft or rod and it has been found that in use the O-ring tends to twist and under conditions of stress the O-ring will actually twist and become extruded along the reciprocating shaft or rod or out over the backup rings. Obviously, this leads to rapid breakdown in the seal and unwanted leakage of the fluid being handled. The seal arrangements of this type are shown in U.S. Pat. Nos. 2,973,978, issued Mar. 7, 1961 and 3,171,334, issued Mar. 2, 1965.

The disadvantages encountered with O-ring seals can be avoided to a certain extent by using a bearing material such as Teflon which is capable of allowing sliding contact under pressure. Such a device is disclosed in U.S. Pat. No. 2,905,489, issued Sept. 2, 1959. In this arrangement, however, rubber-like sealing rings are in contact with the reciprocating or turning shaft and again twisting and unwanted extrusion can occur leading to breakdown in the seal. In this arrangement a U-shaped member facing in the longitudinal direction of the shaft receives a flexible sealing ring which is urged into the U-shaped channel ring in response to the back pressure. This variable pressure loading causes continual flexing and unflexing of the rubber-like sealing ring and the relative movement between the sealing ring and the channel member causes eventual wear and failure of the seal.

Annular shaft or rod seals are extremely critical in devices for dispensing or metering fluids particularly liquids with a high degree of accuracy.

Obviously, if there is any leakage of the fluid being dispensed or metered through the seal, then the accuracy of the device is severly impaired. Because of the lack of completely efficient seals, dispensing and metering devices with a high degree of accuracy are not available.

The present invention, therefore, provides a positive dispensing displacement device with an extremely high degree of accuracy and can thus be used in chemical, analytical, pharmaceutical and medical applications where extremely fine accuracy is required.

SUMMARY

The positive displacement device of the invention comprises:
a. housing means defining a fluid intake and discharge chamber;
b. seal housing means adjacent said housing means;
c. piston means adapted to reciprocate in said seal housing means and said fluid intake and discharge chamber;
d. seal means adapted to prevent the flow of fluid from said fluid intake and discharge chamber to said seal housing means, the seal means being adjacent the fluid intake and discharge chamber and having first ring means in positive sliding sealing contact with said piston means and second ring means compressively positioned between the first ring means and the seal housing means to urge the first ring means against the piston means at a right angle to its direction of travel;
e. means to reciprocate said piston means in said fluid intake and discharge chamber and said seal housing means; and
f. valve means in communication with said fluid intake and discharge chamber adapted to allow fluid to flow into and/or from said chamber in response to the movement of said piston means therein.

In a preferred embodiment, the seal means includes a polymeric channel or L-shaped ring which surrounds the shaft and an O-ring positioned in the channel of the first ring in contact with the seal housing. The preferred material for the channel or L-shaped ring is a halogenated hydrocarbon polymer such as Teflon or Kel-F.

DESCRIPTION OF THE DRAWING

The present invention will be more fully understood from the following description taken in conjunction with the accompanying drawing, wherein:

FIG. 1 is a sectional view illustrating a preferred embodiment of the invention for a positive displacement dispensing device;

FIG. 2 is a sectional view partly broken away of an alternate embodiment in the construction of the dispensing device shown in FIG. 1;

FIG. 3 is a sectional view partly broken away showing a further alternate embodiment in the construction of the dispensing device shown in FIG. 1.

FIG. 4 is a sectional view partly broken away showing an alternate embodiment of the seal means of the invention; and FIG. 5 is a sectional view partly broken away of a further alternate embodiment of the seal means of the invention.

DESCRIPTION

Referring now to the drawing and in particular to FIG. 1, the device of the invention is shown to include a housing 10 which defines a fluid intake and discharge chamber 16. Seal housing 12 is located adjacent the chamber housing 10. The piston 22 is adapted to reciprocate or slide in the seal housing 12 and in the chamber 16. As can be seen from FIG. 1 the chamber 16 has a diameter greater than the diameter of the piston 22. A seal 1 is provided to prevent the flow of fluid from chamber 16 into the seal housing 12 which defines the chamber 18 in which the piston reciprocates with clearance. The seal 1 is adjacent the chamber 16 has a first ring 54 in positive sliding sealing contact with the piston 22 and a second ring 52 which is compressively positioned between the first ring 54 and the seal housing 12 to urge the first ring 54 against the piston 22 at a right angle to its direction of travel.

Guide means 2 is spaced apart and rearward of the seal 1. In this preferred embodiment the guide 2 has the same construction as the seal 1 and is positioned in the seal housing 12. Alternate constructions for the seal 1 and for the guide 2 are shown in FIGS. 2–5 described below.

It is preferred that the seal and guide means 1 and 2 be spaced apart a distance at least equal to or greater than the diameter of the piston 22. Thus, $d_2$ is always equal to or greater than $d_1$.

Means are provided to reciprocate the piston 22 in the chamber 16 and the seal housing 12. The means to reciprocate the piston 22 is shown diagrammatically by box 26 which has an appropriate legend therein.

To complete the structure and to provide protection for the surface of the piston 22 a rear housing 14 is attached to the seal housing 12 and has an internal chamber 20 in which the piston 22 with rod 24 which connects the piston 22 to the reciprocating means 22, move. It should be noted that the rod 24 and piston 22 can also be rotated if desired at the same time it is reciprocated back and forth. The guide 2 can also be positioned in housing 14 if desired rather than in seal housing 12.

A dust filter or annular seal 25 is provided about the rod 24 in the rear housing 14 again to maintain the surface integrity of the piston 22 and to prevent foreign matter from working its way forward into the device which would impair the surface finish of the piston 22.

A valve 30 communicates with the chamber 16 and is adapted to allow fluid to flow into the chamber 16 via conduits 34 and 32 and out of the chamber 16 via conduits 32 and 36 and response to the movement of piston 22 in the chamber 16. The intake, neutral and discharge modes of the device are controlled by rotating the valve handle 40 which rotates valve member 38 into register with conduits 34 or 36 depending on the desired function of the valve. The three way valve construction shown in FIG. 1 is desirable in that it provides a means for maintaining a system completely full of a liquid or fluid which is being dispensed or metered.

In FIG. 2, the seal means 1 in an alternate embodiment is shown to include a first annular ring 54 in positive sliding sealing contact with the piston 22 and a second ring compressively positioned between the first ring 54 and the seal housing 12. The second ring is a composite O-ring including an annular spring 59 with a polymeric material 58 such as Teflon surrounding the annular spring 59. Spaced apart from the seal means 1 is guide ring 2 which is in sliding contact with the piston 22.

In FIG. 3 a similar structure is shown as in FIG. 2 wherein the seal means includes annular channel ring 54 and O-ring 52 is in FIG. 1. Guide means 2 is a composite O-ring in sliding contact with the piston 22 and spaced rearward of the seal means 1. Guide ring 2 is a composite O-ring as utilized in the seal means 1 of FIG. 2.

FIG. 4 shows a further embodiment of the seal means 1. Here a generally L-shaped annular ring 54' replaces the annular channel 54 and is utilized with an O-ring 52 as in the device shown in FIG. 1. The L-shaped ring 54' is positioned between the housing 10 and the seal housing 12 and an annular sealing member such as the O-ring 28 shown in FIG. 1 can be used in conjunction with the L-shaped ring 54' to ensure proper sealing between the two housings 10 and 12. The L-shaped ring 54' has the advantage that the housings 10 and 12 can be pressure sealed by the upright portion of the ring. If desired a similar construction as shown in FIG. 4 can be used for the guide means 2 with the upright portion of the L-shaped ring 54 between the housings 12 and 14.

In FIG. 5 a further alternate embodiment is shown wherein housing 60 defines chamber 16 and the seal housing. The seal means 1 is inverted as compared to the seal means shown in FIG. 1 and the first ring 54 is in positive sliding sealing contact with the interior of chamber 16 and the second ring 52 is compressively positioned between the first ring 54 and the piston 22, the urge ring 54 against the interior of chamber 16 at a right angle to the direction of movement of the piston 22. To accommodate the seal means a recess is provided in the piston 22 adjacent the head thereof as shown. In the embodiment shown in FIG. 5 guide means spaced rearward of the seal means can be utilized as shown in FIG. 1 and can have any of the constructions shown in FIGS. 1–4 for the seal means or the guide means. It should be noted also that the seal means and guide means shown in FIGS. 1–5 can be utilized in any combination desired so long as the seal means includes a first ring in sliding contact with the piston and a second ring compressively positioned between the first ring and the seal housing.

Returning to FIG. 1, it is preferred that the device of the invention be placed in a generally upright position with the housing means 10 over the seal housing means 12 for operation as indicated by the arrow labeled U. The reason for this will become evident from the description of the operation of the device which appears below.

If desired second valve means 30' can communicate with chamber 16 via conduit 34'. The valve 30' is adapted to allow fluid to flow into the chamber 16 in cooperation with the valve means 30 as is more fully described below.

The device of the invention can also be used in tandem to provide for versatility in operation. Such a tandem arrangement could employ a common chamber 16 as shown diagrammatically in FIG. 1 by the box labeled D representing the device of the invention which utilizes the chamber 16 as represented by the dotted line.

The valves 30 and 30' can be operated manually, electrically or electronically controlled to position the valve in the desired input or output position. Other valves such as flapper valves or four-way valves can also be used as are known in the art.

The piston 22 and rod 24 can be reciprocated (and rotated if desired) by any number of means. For example, the piston 22 can be reciprocated manually, by solenoids, rotary solenoids, electric motors, by levers, by gear trains or by precision lead screw and nut and the like. Any of these can be motor driven and the length or number of strokes of the piston 22 can be programmed and/or counted using conventional mechanical stops or electronic devices. The linear movement of the piston 22 can also be monitored and/or programmed using conventional electronic pulse counting devices.

The annular ring members 54 and 54' which are in positive sliding contact with the piston 22 present a flat annular surface which surrounds the piston 22 and which is in positive sliding contact therewith. The annular rings 54 and 54' are compressively urged against the piston 22 at right angles to its direction of travel by O-rings 52 positioned between the annular rings 54 and the seal housing 12.

It should be noted that the upper portion of the annular channel rings 54 in FIG. 1 opposite the flat surface which is in sliding contact with the piston 22 does not contact the seal housing 12. The arrangement of rings 52 and annular channel rings 54 is such that the pressure against the piston 22 is predetermined and selected to prevent the flow of fluid from the chamber 16 into the annular space 18 and can be geared to the operating conditions of the dispensing device. The several housings 10, 12 and 14 are conveniently bolted together as shown in FIG. 1 and an O-ring static seal 28 can be provided between housing 10 and 12 if desired. The housings 10 and 12 can be integrally formed when using seals and guides as shown in FIGS. 1–3.

The annular rings 54 and 54' are made of a non-metallic bearing material and are preferably made of a polymeric material such as an halogenated hydrocarbon polymeric material. Examples of such materials include Teflon, Kel-F and the like. Additives may be present in the annular rings 54 and 54' to increase the sliding efficiency of the positive sliding contact between the rings and the piston 22. Examples of such fillers include graphite, molybdenum disulfide and the like.

In operation, piston 22 is pulled backwards by means 26 to a porition at the rear portion of the chamber 16 forward of or at the seal 1. The valve 30 is in the position shown in FIG. 1 and the rearward movement of the piston 22 causes the chamber 16 to fill up with a fluid (a gas or liquid) from a reservoir or source of fluid (not shown).

When the device of the invention is in the preferred vertical or upright position, air or gas bubbles (when handling a liquid) will rise to the top or valve end of chamber 16 and can be expelled therefrom by advancing the piston a short distance ($S_1$ in FIG. 1 for example) with the valve still in the fill or intake position shown in FIG. 1. Following this the valve 30 is rotated to a neutral position. Under optimum conditions no air or gas bubbles should enter chamber 16 during the filling operation. However, in practice, such bubbles do appear and even though in small amounts, they must be expelled to insure accuracy for the device. Thus, in the invention, entrained bubbles can be tolerated and effectively excluded from chamber 16 before dispensing or metering out a liquid.

When operating vertically, the natural rise of bubbles can be taken advantage of without the need of a prestroke $S_1$ by using valve 30' (FIG. 1) communicating with chamber 16 on an upward slope via conduit 34'. Valve 30 is placed in the fill mode as shown in FIG. 1 and liquid from a suitable source or reservoir feeds into chamber 16 via valve 30' and when full, overflows through valve 30 (conduits 32 and 34) and flows back to the same source of liquid that feeds valve 30'.

Referring again to FIG. 1, to dispense a fluid from the chamber 16 the valve member 38 is rotated from a neutral position to bring conduits 32 and 36 into register and the piston 22 is advanced towards the valve 30. The length of the stroke or forward travel of the piston 22 is predetermined by the means 26. When the desired amount of fluid is dispensed from the chamber 16 the valve then is rotated back to the input mode as shown in FIG. 1 and the piston 22 is withdrawn to replenish the fluid in the chamber 16. The piston 22 can be advanced step-wise to dispense a fluid in several predetermined portions using a single overall forward stroke with pauses or stops. Thus, the term "reciprocate" is intended to include a single complete fill and discharge stroke of piston 22 or a fill and step-wise discharge stroke.

The piston 22 is preferably precision machined to insure sealing contact to a close tolerance and a specific surface finish. A suitable finish falls in the range of an 8 to 16 micro inch finish.

The device of the invention can be used as a positive displacement dispensing and/or metering device or as a positive displacement pump. It is especially useful where extremely high accuracy is required in dispensing of fluids in predetermined amounts. Thus, the device of the invention finds particular utility in the chemical, analytical (e.g. gas chromatography), pharmaceutical and medical fields where extremely high accuracy is demanded in the dispensing of fluids. The invention is especially useful as a dispensing device in that it provides a high degree of accuracy in metering fluids. Thus, for example, the outlet 36 of valve 30 in FIG. 1 can be connected to an aliquot/mixing device as are known in the art wherein a predetermined volume of liquid can be withdrawn from a source by moving piston 22 down with the outlet open and the system full of the desired mixing liquid. The aliquot mixing device is then removed from the liquid and the desired amount of withdrawn liquid and mixing liquid is then discharged by raising or advancing piston 22 with outlet 36 open.

Referring again to the drawing and in particular to FIG. 4 thereof, the particular seal construction shown can be used as a sealing device for reciprocating and/or rotating shafts or pistons in general including not only the device of the invention but also hydraulic devices, compresses and the like. Thus the shaft sealing device in this context comprises seal housing 12 surrounding shaft or piston 22. The sealing means includes L-shaped ring 54' in positive sliding sealing contact with the piston with the upright portion of the ring 54' at a right angle to the piston. The second ring means shown is an O-ring 52 which is radially compressively positioned between the L-shaped ring 54' and the seal housing 12. A unique feature of this construction resides in the fact that the O-ring 52 exerts a radial force against the L-shaped ring 54' so that the ring is urged against the piston 22 and also against the housing 10. When using a polymeric material for the ring 54' such as Teflon, the radial force exerted by the O-ring 52 causes cold flow in both the longitudinal and transverse directions with respect to the piston 22. This promotes and ensures a very effective positive seal. The upper portion of the L-shaped ring 54 can abut the housing 12 as shown or it can be shorter leaving an open space between the ring 54 and the housing 12. If desired the cut-out portion to accommodate the upright portion of the ring 54' can be in the housing 10 or the entire cut-out for the seal construction can be in an integral housing such as shown in FIG. 5 for example.

What is claimed is:
1. Positive displacement device comprising
   a. housing means defining a fluid intake and discharge chamber;
   b. seal housing means adjacent said housing means;
   c. piston means having a constant diameter which is smaller than the diameter of said intake and discharge chamber such that said piston reciprocates in said chamber with complete clearance without contacting said chamber and said piston being further adapted to reciprocate in said seal housing means with clearance in contact with seal and guide as defined below;

d. combined bearing and seal means adapted to prevent the flow of fluid from said fluid intake and discharge chamber to said seal housing means, said seal means being adjacent said chamber and having a polymeric channel-shaped ring presenting a flat annular surface which surrounds said piston in positive sliding sealing and bearing contact with said piston means and an O-ring compressively positioned between the channel ring and the seal housing means to urge the channel ring against the piston means at a right angle to its direction of travel;

e. guide means positioned in the seal housing means and spaced rearward of said combined bearing and seal means, said guide means having a polymeric channel shaped ring presenting a flat annular surface surrounding said piston in positive sliding contact therewith and an O-ring compressively positioned between the channel ring and the seal housing means to urge the channel ring against the piston means at a right angle to its direction of travel, said seal means and said guide means being spaced apart a distance equal to or greater than the diameter of the piston means;

f. means to reciprocate said piston means in said fluid intake and discharge chamber and said seal housing means, said piston annularly contacting solely said spaced apart seal and guide means in said seal housing means; and g. valve means in communication with said fluid intake and discharge chamber adapted to allow fluid to flow into and/or from said chamber in response to the movement of said piston means therein.

2. Device of claim 1 wherein said device is placed in generally upright position with the housing means over the seal housing means for operation.

3. Device of claim 1 wherein the channel ring is in positive sliding sealing contact with the interior of said chamber and the O-ring is compressively positioned between the channel ring and the piston means to urge the channel ring against the chamber interior at a right angle to the direction of movement of the piston means.

4. Device of claim 1, wherein second valve means are provided in communication with said chamber adapted to allow fluid to flow into said chamber in cooperation with said valve means.

5. Device of claim 1 wherein the channel-shaped ring is made of a halogenated hydrocarbon polymer.

6. Device of claim 1 wherein the channel ring is an L-shaped ring with the upright portion thereof at a right angle to said piston and the O-ring ring is radially compressively positioned between the L-shaped ring and the seal housing means to radially urge the L-shaped ring against the piston.

* * * * *